US008828089B1

(12) United States Patent  (10) Patent No.: US 8,828,089 B1
Perez et al.  (45) Date of Patent: Sep. 9, 2014

(54) AUGMENTING AN ACETABULAR IMPLANT SITE

(75) Inventors: Alvin Perez, Ringwood, NJ (US); Brandon J. Black, Hoboken, NJ (US); James D. Macintyre, Greenwood Lake, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 239 days.

(21) Appl. No.: 12/834,447

(22) Filed: Jul. 12, 2010

(51) Int. Cl.
    *A61F 2/34* (2006.01)
(52) U.S. Cl.
    USPC .......................................... 623/22.21; 606/91
(58) Field of Classification Search
    USPC .......... 623/17.18, 20.16, 22.12, 22.15, 22.17,
              623/22.18, 22.19, 22.21–22.39, 23.4, 23.43,
                          623/23.47; 606/71, 91, 280–285, 328
    See application file for complete search history.

(56) References Cited

U.S. PATENT DOCUMENTS

| 5,176,711 | A | | 1/1993 | Grimes |
| 6,004,353 | A | | 12/1999 | Masini |
| 6,007,536 | A | * | 12/1999 | Yue .................................. 606/71 |
| 6,162,257 | A | | 12/2000 | Gustilo et al. |
| 6,340,370 | B1 | * | 1/2002 | Willert et al. .............. 623/22.38 |
| 6,840,959 | B2 | | 1/2005 | Treacy et al. |
| 7,090,676 | B2 | | 8/2006 | Huebner et al. |
| 7,291,177 | B2 | | 11/2007 | Gibbs |
| 7,293,900 | B1 | | 11/2007 | Lee |
| 7,537,618 | B2 | | 5/2009 | Collazo |
| 7,628,816 | B2 | | 12/2009 | Magerl et al. |
| 7,691,145 | B2 | | 4/2010 | Reiley et al. |
| 7,695,473 | B2 | | 4/2010 | Ralph et al. |
| 2006/0089648 | A1 | * | 4/2006 | Masini ........................... 606/69 |
| 2007/0129809 | A1 | * | 6/2007 | Meridew et al. ........... 623/22.32 |
| 2009/0088864 | A1 | * | 4/2009 | Lewis et al. ................ 623/22.21 |

* cited by examiner

*Primary Examiner* — David Isabella
*Assistant Examiner* — Suba Ganesan
(74) *Attorney, Agent, or Firm* — Arthur Jacob (57) ABSTRACT

A method and an acetabular augment are disclosed for compensating for a deficiency encountered in natural bone at an implant site wherein an acetabular component of a prosthetic hip implant is to be implanted within a prepared acetabulum during a hip arthroplasty. A buttress member of an acetabular augment is placed at a selected angular position relative to an affixation member of the acetabular augment, as determined by a trialing procedure in which a trial buttress member is placed at the deficiency while a trial affixation member is placed upon natural bone at the implant site to determine a trial relative angular position between the trial buttress member and the trial affixation member of a trial acetabular augment located at the implant site. The relative angular position between the buttress member and the affixation member then is selected to mimic the trial relative angular position. The location of the trial acetabular augment is marked, and the trial acetabular augment is removed. The acetabular augment then is secured in place at the implant site, at the marked location, to mimic the location of the trial acetabular augment and place the buttress member at the deficiency, with the affixation member placed upon natural bone at the implant site.

25 Claims, 9 Drawing Sheets

AUGMENTING AN ACETABULAR IMPLANT SITE

The present invention relates generally to augmenting an acetabular implant site to compensate for a deficiency encountered in the natural bone at the implant site and pertains, more specifically, to a system of implements and acetabular augmentation components, and methods for implanting an augment component at an acetabular implant site.

Over the many years during which hip arthroplasty has been practiced, improvements in both prosthetic implant components and surgical techniques have been developed toward accomplishing an appropriate and effective end result while minimizing patient trauma arising out of the conduct of an implant procedure. Very often, because of the difficulty of determining beforehand, the true nature of conditions existing at an implant site, a surgeon must compensate for these conditions when encountered during the course of the surgical procedure itself, presenting a situation where the surgeon must act quickly and decisively in order to complete an accurate and effective implantation while reducing the trauma to which the patient is subjected. This is especially true in connection with a revision procedure where it is difficult, if not impossible, to predict the extent of bone deficiency which will be encountered at the revision site during the course of the procedure. In practice, where deficiency of the natural bone at an implant site is found to be extensive, and perhaps even more extensive than anticipated, it becomes important to enable the surgeon to compensate for such conditions intra-operatively, and to do so quickly and effectively. To that end, it has been suggested that a range of augmentation components be made available for selection by the surgeon to compensate for bone deficiencies encountered during hip arthroplasty. However, for the most part, the choices offered to the surgeon by currently available augmentation components and methods are relatively time-consuming and require compromises with respect to accuracy of the end result.

The present invention provides a surgeon with multiple options for addressing a wide range of bone deficiencies encountered at acetabular implant sites, enabling a simplified procedure that quickly and effectively compensates for these deficiencies, with minimal patient trauma. As such, the present invention attains several objects and advantages, some of which are summarized as follows: Provides a system that enables a surgeon to select optimum compensation for an acetabular bone deficiency encountered at a particular acetabular implant site, and to do so intra-operatively, with increased accuracy, ease and dispatch, so as to minimize patient trauma; enables quick and effective compensation for acetabular bone deficiencies as an alternative to current procedures which require time-consuming preparation and use of structural allografts; provides a modular system for augmenting natural bone at an acetabular implant site during hip arthroplasty to compensate for deficiencies encountered in the natural bone at the implant site and thereby accommodate the needs of a particular patient accurately, without requiring a specific, custom-created implant component; enables the use of any of a wide range of currently available acetabular components, at an implant site augmented to compensate for conditions encountered at a particular implant site; expedites the completion of a hip arthroplasty, with increased ease and effectiveness, where augmentation of an acetabular implant site is necessary to compensate for conditions encountered at the implant site, and especially during a revision procedure; reduces trauma created by the conduct of hip arthroplasty, thereby promoting greater patient comfort and safety; promotes confidence on the part of an orthopedic surgeon in the accomplishment of a highly accurate, effective hip arthroplasty; conserves time and expense in completing an accurate and effective hip arthroplasty; provides an acetabular augmentation system having a high degree of versatility and exhibiting exceptional performance over an extended service life for encouraging widespread adoption and use.

The above objects and advantages, as well as further objects and advantages, are attained by the present invention which may be described briefly as an acetabular augment for compensating for a deficiency encountered in natural bone at an implant site wherein an acetabular component of a prosthetic hip implant is to be implanted within a prepared acetabulum during a hip arthroplasty, with an outer surface of the acetabular component engaged with the prepared acetabulum along an acetabular envelope, the acetabular augment comprising: a buttress member having a buttress surface with a surface contour configuration complementary to a corresponding portion of the acetabular envelope; an affixation member having an affixation surface for affixing the affixation member to natural bone adjacent the prepared acetabulum; and a coupling arrangement for coupling the buttress member with the affixation member, the coupling arrangement including coupling elements on the buttress member and on the affixation member for securing the buttress member to the affixation member with the affixation surface at a selected angular position relative to the buttress surface so as to place the buttress surface in juxtaposition with the acetabular envelope upon affixation of the affixation surface to the natural bone adjacent the prepared acetabulum, whereby the buttress surface will be located to supplement the prepared acetabulum for reception of the acetabular component along the acetabular envelope.

In addition, the present invention provides a method of compensating for a deficiency encountered in natural bone at an implant site wherein an acetabular component of a prosthetic hip implant is to be implanted within a prepared acetabulum during a hip arthroplasty, with an outer surface of the acetabular component engaged with the prepared acetabulum along an acetabular envelope, the method comprising: providing a trial buttress member having a trial buttress surface with a surface contour configuration complementary to a corresponding portion of the acetabular envelope; providing a trial affixation member having an affixation surface for engaging natural bone adjacent the prepared acetabulum, the trial affixation member being coupled with the trial buttress member so as to enable selective placement of the trial affixation surface at a selected angular position relative to the trial buttress surface; placing the trial buttress surface in juxtaposition with the acetabular envelope at the deficiency and moving the trial affixation member relative to the trial buttress member to place the trial affixation surface upon the natural bone adjacent the prepared acetabulum while the trial buttress surface is located in position to supplement the prepared acetabulum for effective implantation of the acetabular component along the acetabular envelope; marking the location of the trial affixation member on the natural bone adjacent the prepared acetabulum; determining the angular position of the trial affixation surface relative to the trial buttress surface; providing a buttress member having a buttress surface with a configuration that mimics the trial buttress surface; providing an affixation member having an affixation surface with a configuration that mimics the trial affixation surface; securing the affixation member to the buttress member at a relative angular position matching the angular position determined between the trial affixation surface and the trial buttress surface, to mimic the selected relative angular position between the trial affixation surface and the trial buttress surface; placing the affixation member at the previously marked location of the trial affixation member to locate the buttress surface in juxtaposition with the acetabular envelope at the deficiency; and securing the affixation member and buttress member in place with the buttress surface juxtaposed with the acetabular component and the affixation member affixed to the natural bone adjacent the prepared acetabulum.

Further, the present invention provides a system for use in compensating for a deficiency encountered in natural bone at an implant site wherein an acetabular component of a prosthetic hip implant is to be implanted within a prepared acetabulum during a hip arthroplasty, with an outer surface of the acetabular component engaged with the prepared acetabulum along an acetabular envelope, the system comprising: a trial acetabular augment including a trial buttress member having a trial buttress surface with a surface contour configuration complementary to a corresponding portion of the acetabular envelope, a trial affixation member having an affixation surface for engaging natural bone adjacent the prepared acetabulum, the trial affixation member being coupled with the trial buttress member for selective angular movement relative to one another to enable selective placement of the trial affixation surface at a selected angular position relative to the trial buttress surface; a restraining mechanism for restraining relative angular movement between the trial affixation member and the trial buttress member away from the selected angular position of the trial affixation surface relative to the trial buttress surface; a marking arrangement for establishing a marked location of the trial affixation member on the natural bone adjacent the prepared acetabulum; a first indicator for indicating the selected angular position of the trial affixation surface relative to the trial buttress surface; and an acetabular augment including a buttress member having a buttress surface with a configuration that mimics the trial buttress surface; an affixation member having an affixation surface with a configuration that mimics the trial affixation surface; a coupling arrangement for coupling the affixation member to the buttress member and for securing the affixation member to the buttress member at a relative angular position matching the angular position indicated between the trial affixation surface and the trial buttress surface, to mimic the selected relative angular position between the trial affixation surface and the trial buttress surface; a second indicator for indicating the selected angular position of the affixation surface relative to the buttress surface; a locator arrangement on the acetabular augment for locating the affixation member at the previously marked location of the trial affixation member to locate the buttress surface in juxtaposition with the acetabular envelope at the deficiency; and an affixation arrangement on the acetabular augment for affixing the acetabular augment in place with the buttress surface juxtaposed with the acetabular envelope and the affixation member affixed to the natural bone adjacent the prepared acetabulum.

Still further, the present invention includes a trial acetabular augment for use in compensating for a deficiency encountered in natural bone at an implant site wherein an acetabular component of a prosthetic hip implant is to be implanted within a prepared acetabulum during a hip arthroplasty, with an outer surface of the acetabular component engaged with the prepared acetabulum along an acetabular envelope, the trial acetabular augment comprising: a trial buttress member having a trial buttress surface with a surface contour configuration complementary to a corresponding portion of the acetabular envelope; a trial affixation member having an affixation surface for engaging natural bone adjacent the prepared acetabulum, the trial affixation member being coupled with the trial buttress member for selective angular movement relative to one another to enable selective placement of the trial affixation surface at a selected angular position relative to the trial buttress surface; a restraining mechanism for restraining relative angular movement between the trial affixation member and the trial buttress member away from the selected angular position of the trial affixation surface relative to the trial buttress surface; a marking arrangement for establishing a marked location of the trial affixation member on the natural bone adjacent the prepared acetabulum; and an indicator for indicating the selected angular position of the trial affixation surface relative to the trial buttress surface.

The invention will be understood more fully, while still further objects and advantages will become apparent, in the following detailed description of preferred embodiments of the invention illustrated in the accompanying drawing, in which:

Figure 1:
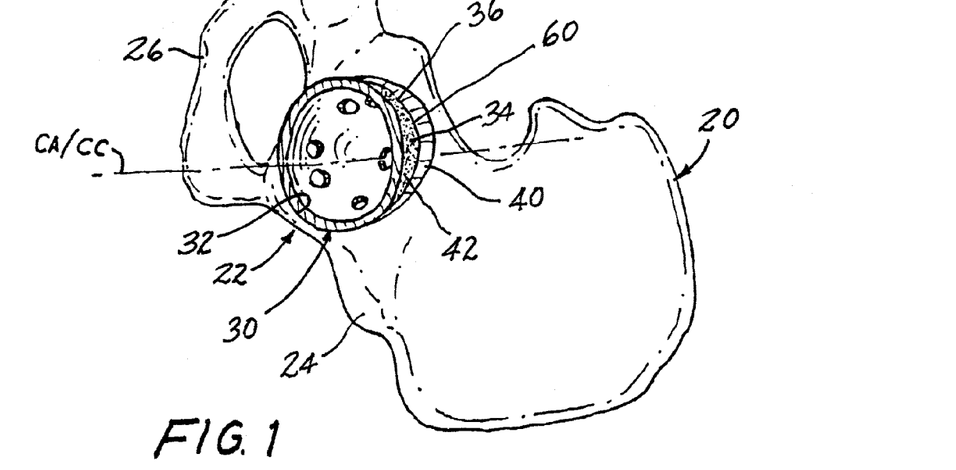
FIG. 1 is a somewhat schematic pictorial view showing an acetabular implant site suffering from a deficiency in the natural bone.
Figure 2:
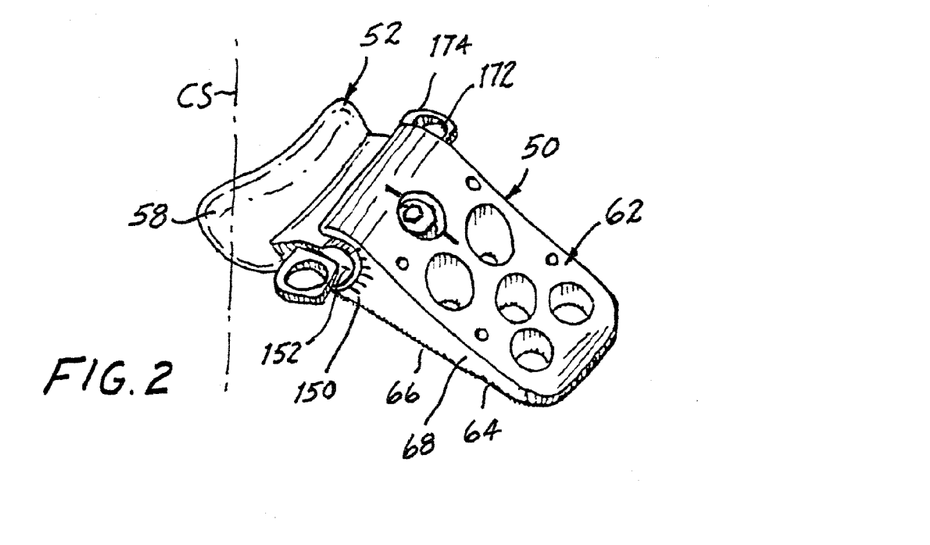
FIG. 2 is a pictorial view of an acetabular augment constructed in accordance with the present invention.

Referring now to the drawing, and especially to FIG. 1 thereof, a pelvic bone is illustrated somewhat schematically at 20 and shows an acetabular implant site 22 located between ilium portion 24 and ischium portion 26 of the pelvic bone 20. An acetabular component of a prosthetic hip implant is shown in the form of a conventional acetabular cup 30 which has been placed in a prepared acetabulum 32 in connection with the conduct of a hip arthroplasty. Acetabular cup 30 has an outer surface 34 which has been fitted into the prepared acetabulum 32 along an acetabular envelope 36, with the central axis CC of the outer surface 34 extending in a longitudinal direction; however, a deficiency in the form of a gap 40 in the natural bone of pelvic bone 20 has been encountered so that a significant portion 42 of the outer surface 34 is exposed, and therefore unsupported, along the acetabular envelope 36, rendering the seating of the acetabular cup 30 somewhat unstable within the prepared acetabulum 32. Gap 40 can be the result of deterioration of the natural bone due to disease or, as frequently is the case, due to a previous hip arthroplasty which now requires revision.

Turning now to FIGS. 2 through 10, as well as with reference to FIG. 1, in order to compensate for the presence of gap 40, and thereby stabilize an accurate seating of acetabular cup 30 within prepared acetabulum 32, the present invention provides an acetabular augment shown in the form of augment 50. Augment 50 includes a buttress member 52 having a buttress surface 54 which extends along an obverse face 56 of a brace 58 of buttress member 52 and follows a surface contour configuration complementary to a corresponding portion 60 of acetabular envelope 36, which portion 60, in turn, is complementary to exposed portion 42 of the outer surface 34 of the acetabular cup 30. In the illustrated embodiment, the surface contour configuration of face 56 is part-spherical and has a central spherical axis CS so as to complement the semi-spherical contour configuration of the outer surface 34 of acetabular cup 30. Augment 50 further includes an affixation member 62 having an affixation surface 64 extending along a basal face 66 of a plate 68 of affixation member 62, the basal face 66 preferably following a substantially planar surface configuration.

Figures 3, 6:
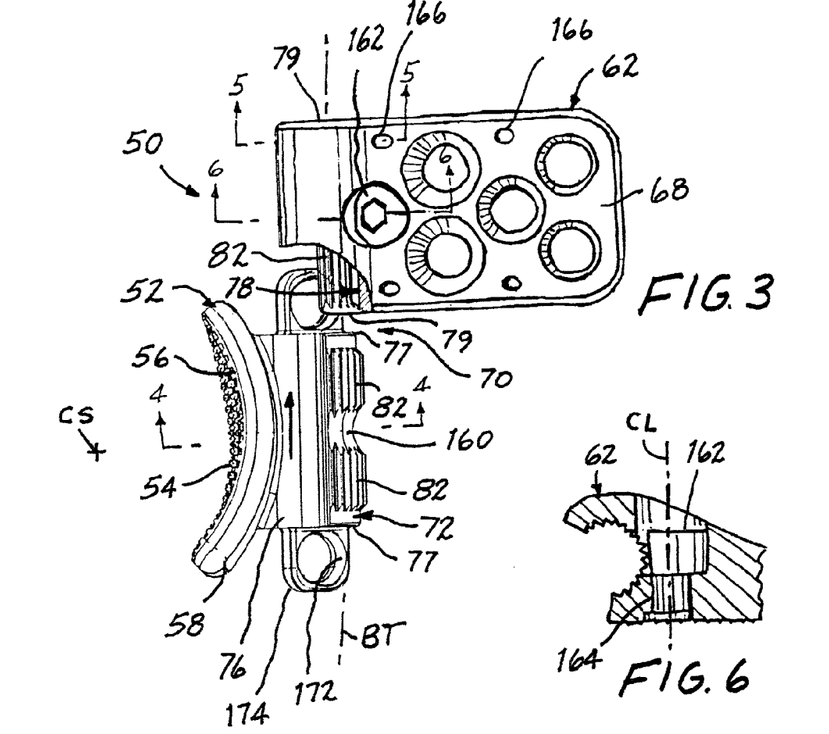
FIG. 3 is an exploded pictorial view of the acetabular augment.
FIG. 6 is a fragmentary cross-sectional view taken along line 6-6 of FIG. 3.
Figure 4:
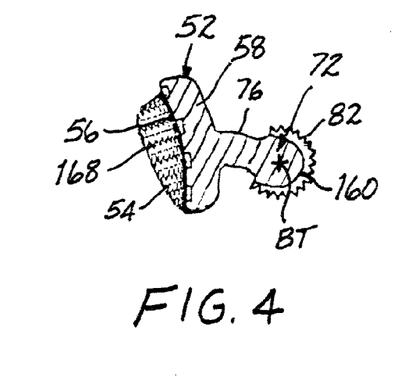
FIG. 4 is a fragmentary cross-sectional view taken along line 4-4 of FIG. 3.
Figure 5:
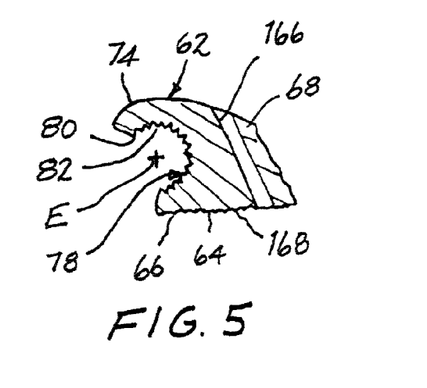
FIG. 5 is a fragmentary cross-sectional view taken along line 5-5 of FIG. 3.

A coupling arrangement for coupling the buttress member 52 with the affixation member 62 is illustrated at 70 and is seen to include a first coupling element in the form of a bar 72 carried by the brace 58 of the buttress member 52, and a second coupling element shown in the form of a bracket 74 carried by the plate 68 of the affixation member 62. Bar 72 is integral with brace 58 of buttress member 52, and preferably is unitary with brace 58, the bar 72 being connected to the brace 58 by a neck 76 such that the bar 72 extends along a transverse axis BT spaced in a lateral direction away from the central axis CS. Bar 72 has a generally part-circular cross-sectional configuration and extends in a transverse direction between opposite bar ends 77. Bracket 74 includes a channel 78 extending along a transverse direction across the bracket 74, between opposite channel ends 79, and having a generally C-shaped cross-sectional configuration complementary to the part-circular cross-sectional configuration of bar 72 and which provides a slot 80 extending in the transverse direction along the length of the channel 78.

Buttress member 52 is assembled with affixation member 62 by aligning bar 72 with channel 78 along an engagement axis E, with neck 76 aligned with slot 80 so that axis BT is aligned with engagement axis E, and then sliding bar 72 along engagement axis E and into channel 78, until the opposite bar ends 77 are brought into juxtaposition with corresponding opposite channel ends 79. For purposes to be described more fully below, bar 72 and channel 78 include complementary connector configurations which engage the buttress member 52 with the affixation member 62 with the affixation surface 64 placed at a selected angular position relative to the buttress surface 54. Thus, the complementary connector configurations are shown in the form of interengageable splined configurations which, upon sliding bar 72 into engagement with channel 78, interengage to establish a selected angular position between the buttress member 52 and the affixation member 62. Each splined configuration includes transversely extending splines 82 which are spaced apart circumferentially about engagement axis E by angular spacings that establish fixed angular increments between adjacent angular positions of the buttress member 52 relative to the affixation member 62. In the illustrated embodiment, the splines 82 are spaced apart circumferentially to establish fifteen degree increments providing six angular positions over a range extending between twenty degrees and ninety-five degrees of relative angular position between the buttress member 52 and the affixation member 62, as illustrated by angle θ in FIGS. 9 and 10, respectively. However, angular increments of another magnitude are feasible, as well as other numbers of angular positions over other ranges of angular positions.

Referring now to FIGS. 11 through 17, and with further reference to FIGS. 1 through 10, with the acetabular cup 30 in place in prepared acetabulum 32, as illustrated in FIG. 1, an implement of the present invention is shown in the form of a trial augment 90 employed for determining the placement of acetabular augment 50 to compensate for the deficiency encountered in the natural bone at the implant site 22, as exemplified by gap 40. In a construction similar to that described above in connection with augment 50, trial augment 90 includes a trial buttress member 92 having a trial buttress surface 94 which follows a surface contour configuration complementary to the outer surface 34 of acetabular cup 30 and, consequently, complementary to acetabular envelope 36, aligned along a longitudinal central buttress axis CB. Trial augment 90 further includes a trial affixation member 112 having a trial affixation surface 114 extending along a trial basal surface 116, preferably following a basal plane. Trial buttress member 92 is joined with trial affixation member 112 by a bar 122 carried by the trial buttress member 92 and engaged with a channel 124 within the trial affixation member 112. Unlike in the assembled buttress member 52 and affixation member 62, bar 122 is journaled for rotation within channel 124, about a transverse axis T, to select a relative angular position between the trial buttress member 92 and the trial affixation member 112 and, consequently, between the trial buttress surface 94 and the trial basal surface 116.

Figure 13:
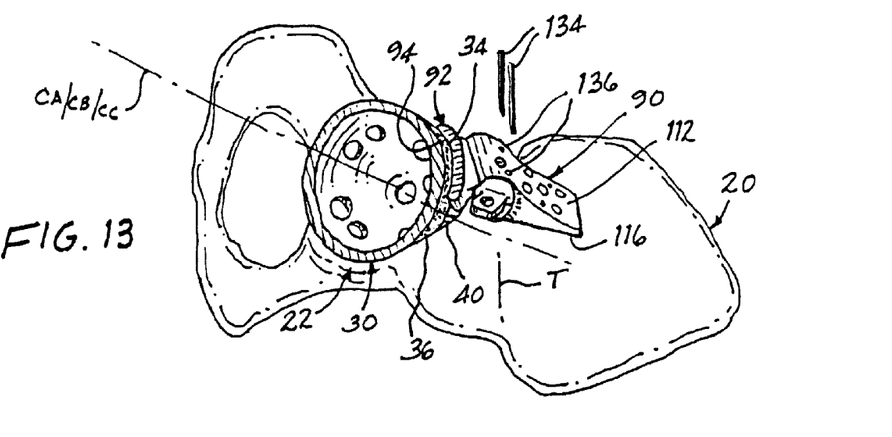
FIGS. 13 through 17 are pictorial views illustrating an acetabular implant site compensation method carried out in accordance with the present invention utilizing a system of the present invention.

The prepared acetabulum 32 has a longitudinally extending predetermined central acetabular axis CA with which the central axis CC of the outer surface 34 of the acetabular cup 30 is aligned upon seating of the acetabular cup 30 within the prepared acetabulum 32. A trialing procedure is initiated by placing the trial buttress surface 94 in juxtaposition with the outer surface 34 of the acetabular cup 30 and, consequently, in juxtaposition with acetabular envelope 36, at the gap 40, such that the central buttress axis CB is aligned substantially with central acetabular axis CA. With the trial buttress surface 94 held in place in the aforesaid position, as illustrated in FIG. 13, the trial affixation member 112 is rotated about transverse axis T, relative to trial buttress member 92, until trial basal surface 116 is seated upon the natural bone adjacent prepared acetabulum 32, as shown at 128 in FIG. 14.

Figure 12:
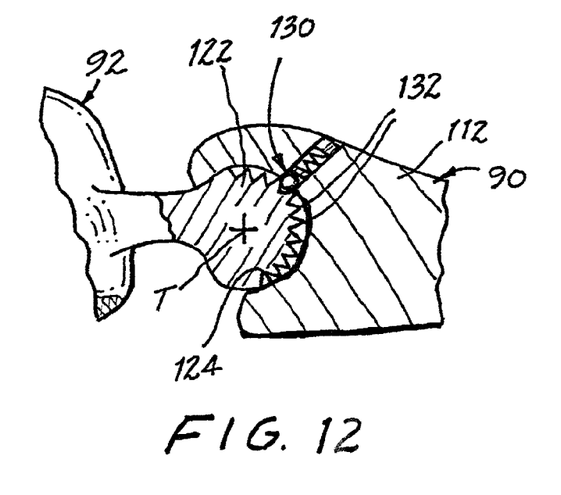
FIG. 12 is an enlarged fragmentary view of a portion of the trial augment, partially in cross-section to show internal details.
Figure 14:
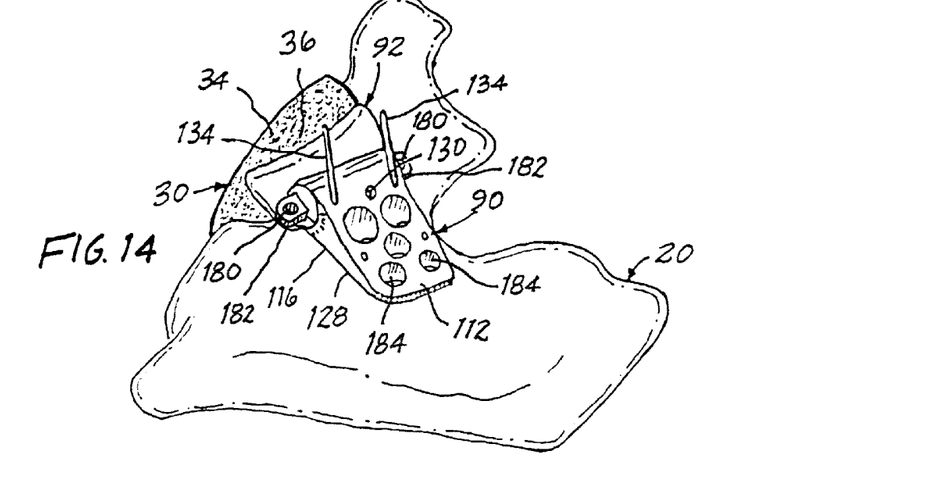

Once the trial basal surface 116 is fully seated upon the natural bone at 128, and with the trial buttress surface 94 juxtaposed with the acetabular envelope 36 at the gap 40, the trial buttress member 92 and the trial affixation member 112 are retained against angular movement relative to one another. While such retention can be accomplished by a restraining mechanism which merely utilizes a frictional fit between bar 122 and channel 124 that will retain the trial buttress member 92 at a selected angular position relative to the trial affixation member 112, enabling only a forced rotation of bar 122 within channel 124 to any selected relative angular position between the trial buttress member 42 and the trial affixation member 112, in a manner more fully described below, a more positive retention is preferred and is shown to be accomplished by a restraining mechanism that employs a ball detent 130 placed within trial affixation member 112 to engage bar 122 between teeth 132 located in bar 122, as illustrated in FIG. 12, and preclude inadvertent rotation of bar 122 of trial buttress member 92 within channel 124 of trial affixation member 112. Teeth 132 are spaced apart circumferentially around bar 122, the circumferential spacing of teeth 132 corresponding to the circumferential spacing between splines 82 about engagement axis E, as described above, such that the trial buttress member 92 and the trial affixation member 112 are movable selectively among fixed increments of rotation corresponding to the fixed increments of relative angular position available between the buttress member 52 and the affixation member 62 of the augment 50, as set forth above. The position of trial affixation member 112 on the natural bone, as indicated at 128, then is marked by passing at least two locator pins 134 through counterpart marking apertures 136 in the trial affixation member 112 and anchoring the locator pins 134 in the natural bone to establish spaced apart locator positions on the natural bone. The trial augment 90 then is removed from the implant site 22, leaving behind the locator pins 134 anchored in the natural bone of pelvic bone 20, as seen in FIG. 14.

Figure 11:
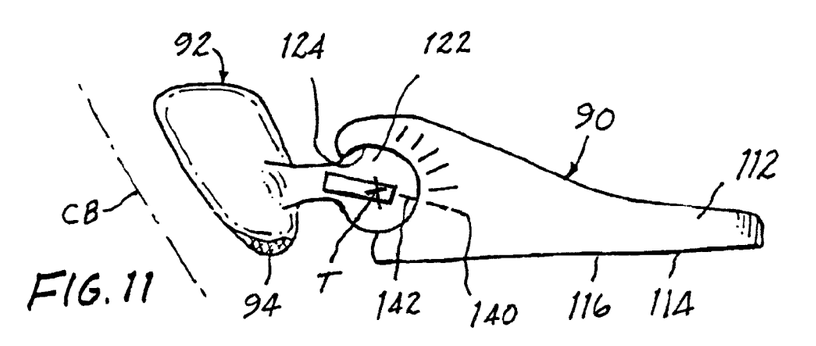
FIG. 11 is a side elevational view of a trial acetabular augment constructed in accordance with the present invention.

As best seen in FIG. 11, the trial buttress member 92 and the trial affixation member 112 bear an indicator which provides an indication of the relative angular positions of the trial buttress member 92 and the trial affixation member 112. Thus, indices are provided in the form of a visible scale 140 placed on the trial affixation member 112 and a visible index mark 142 placed on the trial buttress member 92. The scale 140 is indicative of the fixed increments of relative angular position available between the buttress member 52 and the affixation member 62 of the augment 50, as described above, so that with the trial buttress member 92 and the trial affixation member 112 retained together, as set forth immediately above, the observed position of the index mark 142 will provide observable information needed to set the relative angular position of the buttress member 52 and the affixation member 62 required to compensate for the deficiency at gap 40.

As seen in FIGS. 2, 9, 10 and 15, buttress member 52 and affixation member 62 bear indices which mimic the indices located on the trial buttress member 92 and the trial affixation member 112. Thus, a visible scale 150 on the affixation member 62 corresponds to visible scale 140 on trial affixation member 112, and a visible index mark 152 on the buttress member 52 corresponds to visible index mark 142 on trial buttress member 92. Buttress member 52 then is assembled with affixation member 62, engaging bar 72 with channel 78 along engagement axis E while aligning index mark 152 with scale 150 in accordance with the position of the index mark 142 relative to scale 140, as determined during the trialing process described above, so that the configuration of augment 50, when assembled, will mimic the configuration of the trial augment 90 with respect to the relative angular position of the buttress member 52 and the affixation member 62.

As set forth above, the splines 82 of the augment 50 are spaced apart circumferentially to establish selectable relative angular positions between the buttress member 52 and the affixation member 62 and, more particularly, between the buttress surface 54 of the buttress member 52 and the affixation surface 64 of the affixation member 62. Utilizing the index mark 152 and the scale 150, the buttress member 52 and the affixation member 62 are assembled readily in a relative angular position which mimics that determined by the use of the trialing augment 90 during the trialing procedure, and that relative angular position is fixed securely by the interengagement of the splines 82 upon sliding bar 72 into channel 78, along the transverse engagement axis E. In the illustrated embodiment, the engagement axis E extends substantially parallel to the plane of basal face 66 in the longitudinal direction so as to assure appropriate location and orientation of the buttress surface 54 at the gap 40 upon seating of the affixation surface 64 upon the natural bone adjacent the prepared acetabulum 32. The splined connection provided by interengaged splines 82 not only assures that the buttress member 52 and the affixation member 62 are secured together in a well-defined relative angular relationship, as determined by the trialing procedure, but will remain in rigid securement during an extended service life of augment 50, as well as during the implantation procedure itself.

Figure 7:
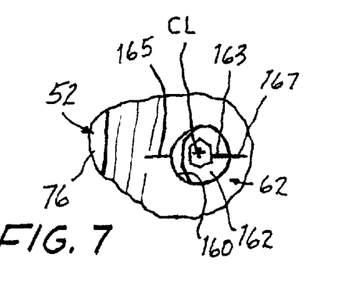
FIG. 7 is a top plan view of the fragment of FIG. 6, with the inclusion of a component part illustrated in FIG. 3.

Once the bar 72 is fully engaged with the channel 78, as described above, a locking arrangement is actuated to preclude further relative sliding movement between the buttress member 52 and the affixation member 62 along axis E and thereby secure together the buttress member 52 and the affixation member 62 in the fully integrated augment 50. The locking arrangement includes respective locking elements on the buttress member 52 and on the affixation member 62, the locking elements being illustrated in the form of a circumferential groove 160 in the bar 72, located intermediate the bar ends 77, and a cam lock 162 mounted in the affixation member 62, as seen at 164 in FIG. 6, for selective rotation about a longitudinal cam axis CL, between an unlocked position, as shown in FIG. 7, wherein the cam lock 162 is retracted from groove 160 for enabling unrestricted sliding movement of the bar 72 within channel 78 to assemble buttress member 52 with affixation member 62, as set forth above, and a locking position, as shown in FIG. 8, wherein the cam lock 162 is advanced for being received within groove 160 to preclude further sliding movement along axis E of bar 72 within channel 78.

Figure 8:
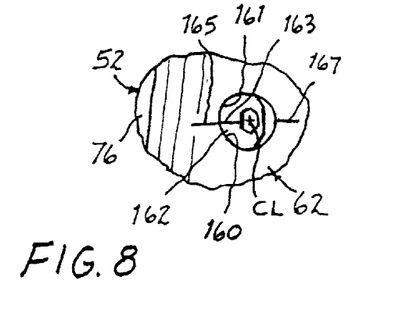
FIG. 8 is a top plan view similar to FIG. 7 and with component parts in another operating position.
Figure 9:
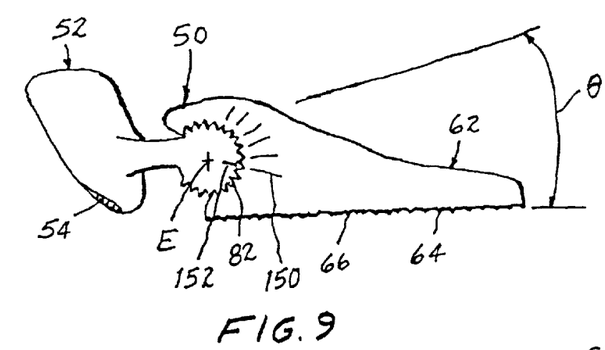
FIGS. 9 and 10 are somewhat diagrammatic side elevational views illustrating a range of adjustment of the relative angular positions of component parts of the acetabular augment.
Figure 10:
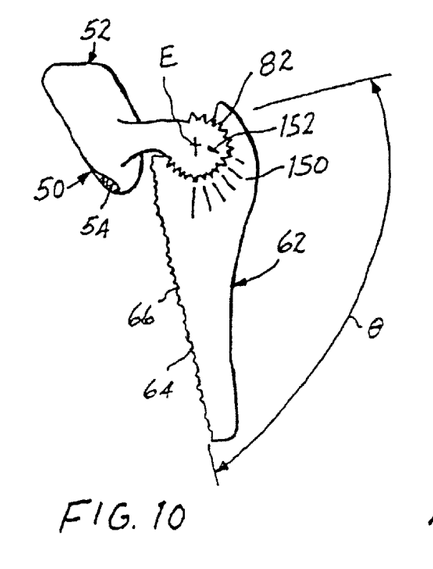

Groove 160 and cam lock 162 are provided with complementary engaging surface configurations, as illustrated at 161 in FIG. 8, such that upon rotation of cam lock 162 into full engagement with groove 160, as indicated by the registration of indicator marks 163 and 165, buttress member 52 and affixation member 62 will be urged together along engagement axis E into precise alignment with one another in the lateral direction. In the unlocked position of cam lock 162, indicator mark 163 is registered with indicator mark 167, as seen in FIG. 7, to indicate the fully unlocked placement of cam lock 162, wherein bar 72 is moved freely into channel 78 for ready assembly of buttress member 52 and affixation member 62. The combination of the interengaged splines 82 and the fully locked position of the cam lock 162 within groove 160 assures that the buttress member 52 and the affixation member 62 are secured together immovably, at the selected angular position relative to one another, and in precise lateral alignment, upon assembly of augment 50 and subsequent completion of the implantation procedure.

Figure 15:
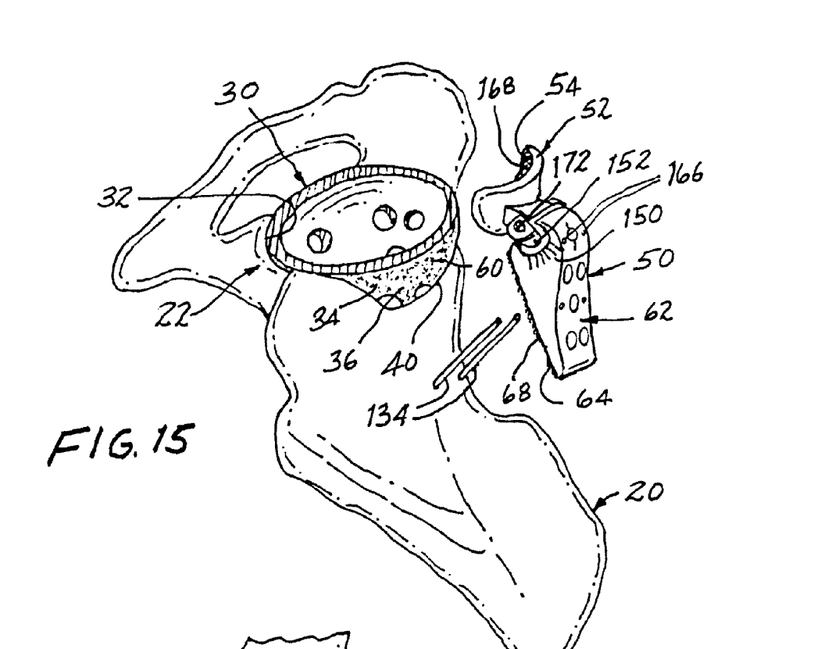
Figure 16:
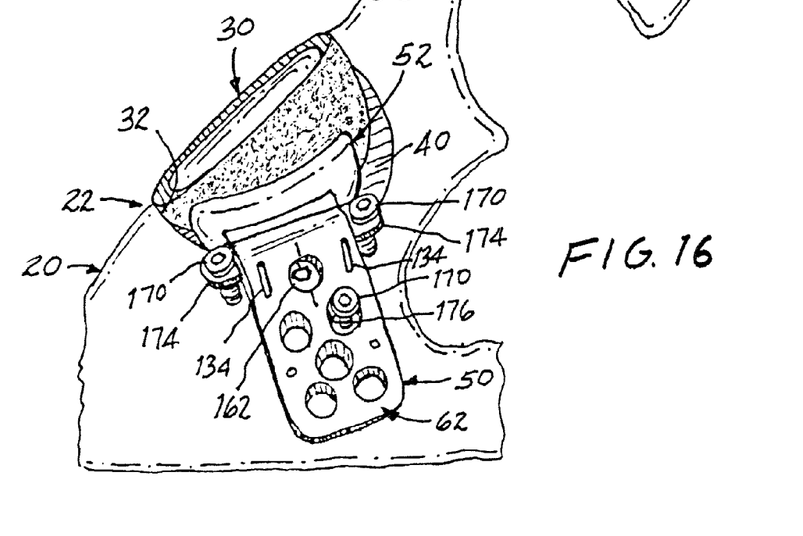

With the buttress member 52 and the affixation member 62 assembled and secured together in the desired relative angular position, within the fully integrated augment 50, the plate 68 of the affixation member 62 is slipped over the previously anchored locator pins 134, as shown in FIGS. 15 and 16, the plate 68 having locator apertures 166 placed at locations corresponding to the locations of marking apertures 136 in trial affixation member 112, and, with the locator pins 134 received within counterpart locator apertures 166, the augment 50 is seated in place at the implant site 22, as seen in FIG. 16. Optionally, one or both of a bone cement and an adhesive may be applied to the buttress surface 54 and to the affixation surface 64, prior to slipping the augment 50 over the locator pins 134. To that end, both the buttress surface 54 and the affixation surface 64 are provided with a surface treatment 168 which facilitates a cement or an adhesive attachment.

Figure 17:
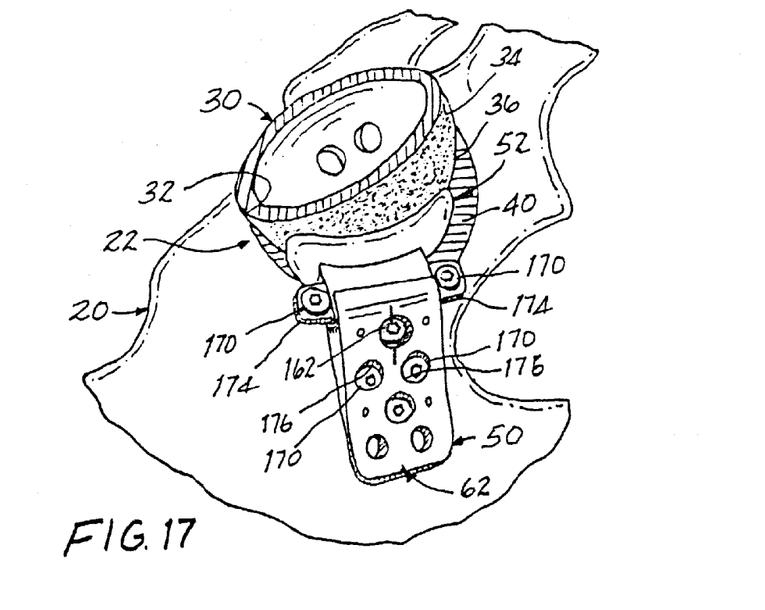

The augment 50 is affixed at the implant site 22 by the insertion of fasteners, here shown in the form of bone screws 170, through fastener openings shown in the form of screw-hole openings 172 provided in tabs 174 carried by the buttress member 52, and through fastener openings shown in the form of screw-hole openings 176 provided in the affixation member 62, as seen in FIG. 16. Trial augment 90 is provided with counterpart simulated screw-hole openings 180 in tabs 182 carried by trial buttress member 92, and counterpart simulated screw-hole openings 184 in the trial affixation member 112, to assist in determining an optimum placement of the augment 50 where sufficient natural bone is available for the reception of appropriate fasteners through screw-hole openings 172 and 176. Once augment 50 is secured in place, locator pins 134 are removed, and the augmentation procedure is complete, as illustrated in FIG. 17.

Figure 18:
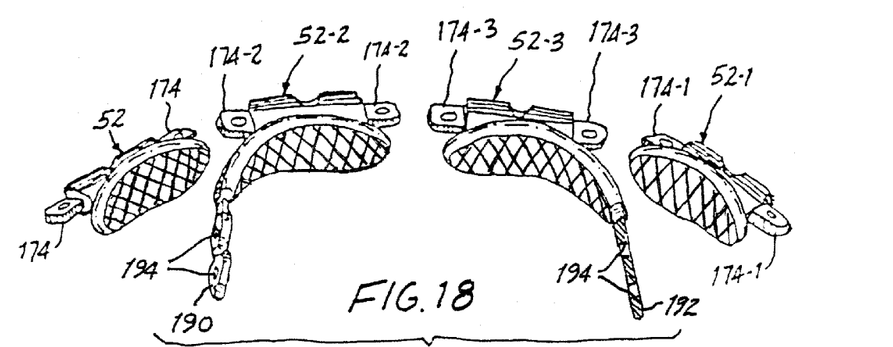
FIG. 18 is a pictorial view illustrating alternate component parts of the acetabular augment.

Turning now to FIG. 18, in addition to buttress member 52, alternate buttress members are interchangeable for assembly with affixation member 62 to accommodate different locations of bone deficiencies which may be encountered at different implant sites. Thus, while buttress members 52, 52-1, 52-2 and 52-3 are configured to address defects located such that tabs 174, 174-1, 174-2 and 174-3 can be affixed to an adjacent ilium portion of a pelvic bone, such as ilium portion 24 of pelvic bone 20, buttress members 52-2 and 52-3 include corresponding further tabs 190 and 192 which extend beyond respective tabs 174-2 and 174-3 to address defects which may not be accommodated only by fasteners passed through tabs 174-2 or 174-3. Thus, tabs 190 and 192 include supplemental screw-holes 194 and can be affixed to an adjacent ischium portion of a pelvic bone, such as ischium portion 26 of pelvic bone 20, the ischium portion providing natural bone suitable for the reception of fasteners extending through corresponding screw holes 194 spaced a distance away from the above ilium portions, thereby enabling a secure affixation of a buttress member 52 to natural bone available at implant site 22. Moreover, these supplemental further tabs 174-2 and 174-3, by virtue of malleable qualities of the material of each buttress member 52-2 and 52-3, are capable of being bent or otherwise deformed into a configuration which will juxtapose the screw holes 194 of a further tab 174-2 or 174-3 with natural bone available adjacent an ischium portion of the pelvic bone appropriate for such affixation, rendering augment 50 highly versatile and very effective. While various configurations are shown in the from of alternate buttress members for accommodating different conditions encountered at an implant site, it is noted that similarly, affixation members of different configurations are feasible to match different conditions encountered at an implant site.

Figures 19, 20:
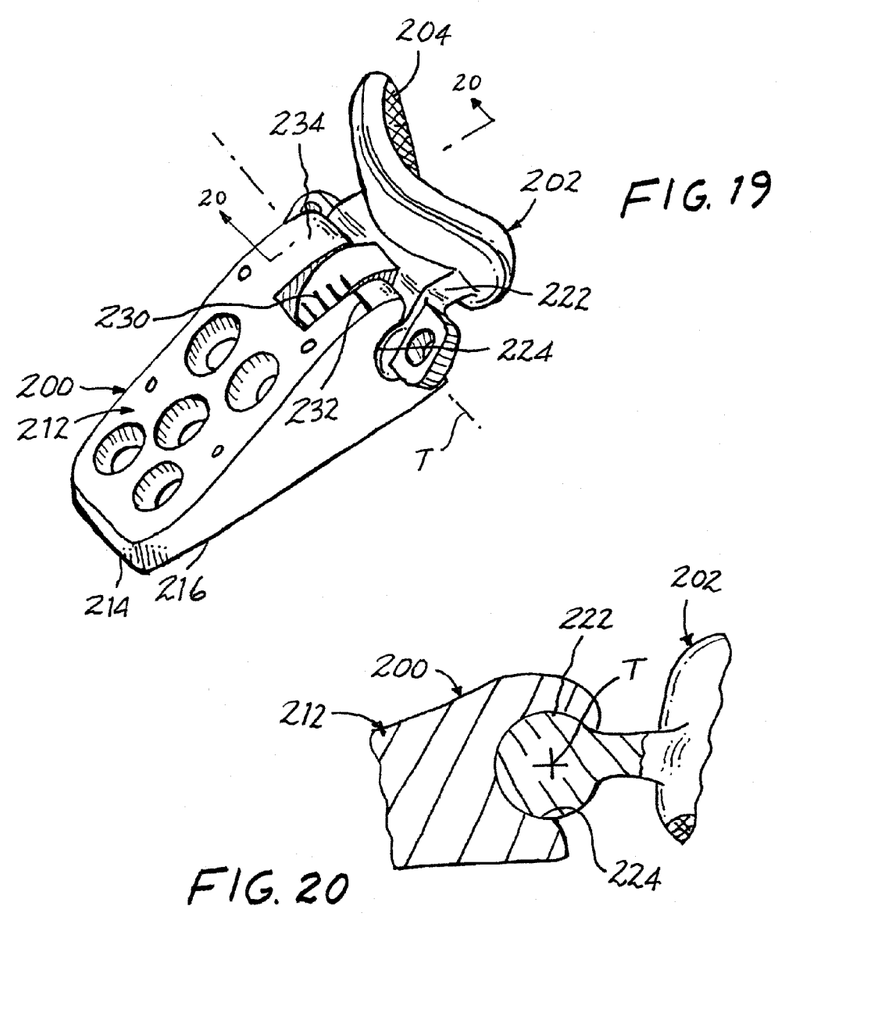
FIG. 19 is a pictorial view illustrating an alternate trial acetabular augment constructed in accordance with the present invention.
FIG. 20 is an enlarged fragmentary cross-sectional view taken along line 20-20 of FIG. 19.

Referring now to FIGS. 19 and 20, as well as with further reference to FIGS. 1 through 17, an alternate trial augment constructed in accordance with the present invention is shown at 200 for employment to determine the placement of acetabular augment 50 in compensating for the deficiency encountered in the natural bone at the implant site 22, as exemplified by gap 40. In a construction similar to that described above in connection with trial augment 90, trial augment 200 includes a trial buttress member 202 having a trial buttress surface 204 which follows a surface contour configuration complementary to the outer surface 34 of acetabular cup 30 and, consequently, complementary to acetabular envelope 36, aligned along longitudinal central buttress axis CB. Trial augment 200 further includes a trial affixation member 212 having a trial affixation surface 214 extending along a trial basal surface 216, preferably following a basal plane.

Trial buttress member 202 is joined with trial affixation member 212 by a bar 222 carried by the trial buttress member 202 and engaged with a channel 224 within the trial affixation member 212. In the present embodiment, bar 222 is journaled for rotation within channel 224, about a transverse axis T, to enable movement of the trial buttress member 202 and the trial affixation member 212 through a range of relative angular positions for selecting an appropriate relative angular position between the trial buttress member 202 and the trial affixation member 212 and, consequently, between the trial buttress surface 204 and the trial basal surface 216, with a friction fit between the bar 222 and the channel 224 providing a restraining mechanism wherein complementary connector configurations on bar 222 and in channel 224 create a frictional biasing force establishing a bias against inadvertent relative angular movement between trial buttress member 202 and trial affixation member 212 away from the selected relative angular position. Indicia in the form of a visible scale 230 on the trial buttress member 202 and a visible index mark 232 on the trial affixation member 212 provide a visible indication of the selected relative angular position between the trial affixation member 212 and the trial buttress member 202. In the present embodiment, the visible indication is located at the top 234 of the trial augment 200, rendering the indication highly visible for a quick and convenient determination of the relative angular position.

Figure 21:
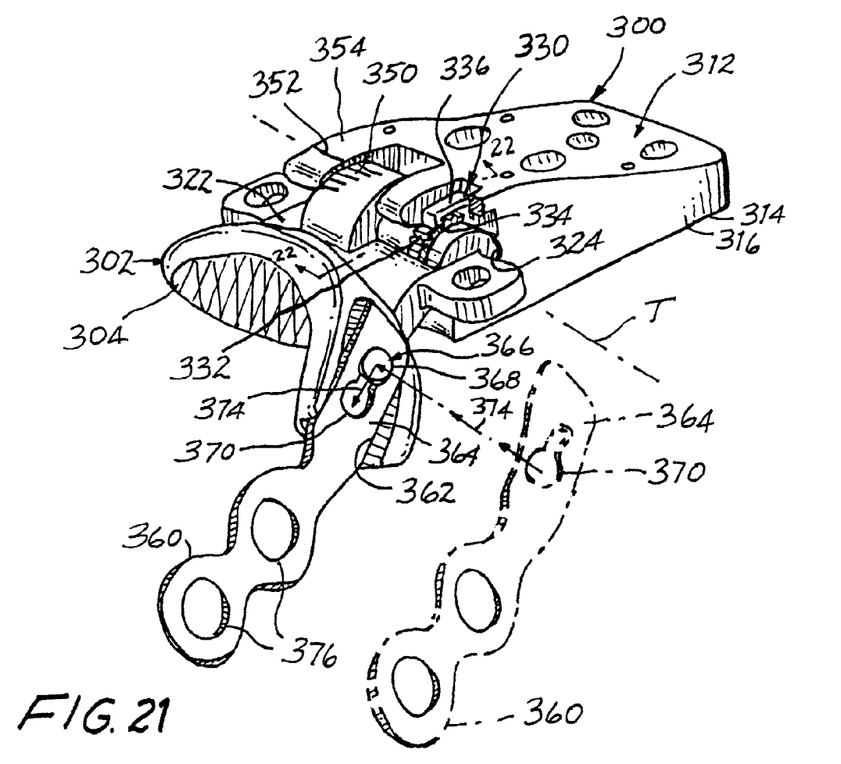
FIG. 21 is a pictorial view illustrating another alternate trial acetabular augment constructed in accordance with the present invention.
Figure 22:
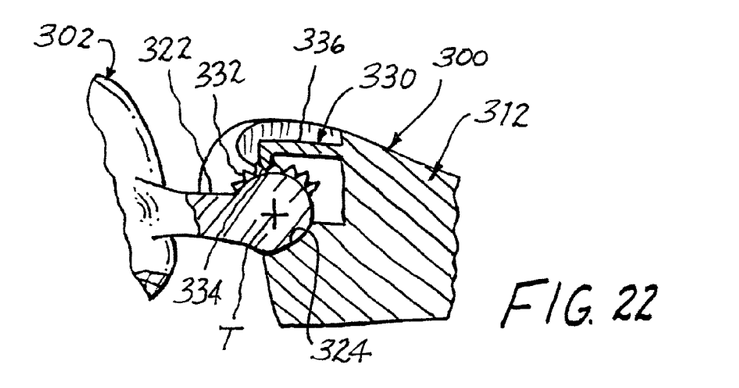
FIG. 22 is an enlarged fragmentary cross-sectional view taken along line 22-22 of FIG. 21.

Turning now to FIGS. 21 and 22, as well as with further reference to FIGS. 1 through 18, another alternate trial augment constructed in accordance with the present invention is shown at 300 for use in determining the placement of acetabular augment 50 to compensate for a deficiency encountered in the natural bone at the implant site 22, as exemplified by gap 40. In a construction similar to that described above in connection with trial augment 90, trial augment 300 includes a trial buttress member 302 having a trial buttress surface 304 which follows a surface contour configuration complementary to the outer surface 34 of acetabular cup 30 and, consequently, complementary to acetabular envelope 36, aligned along longitudinal central buttress axis CB. Trial augment 300 further includes a trial affixation member 312 having a trial affixation surface 314 extending along a trial basal surface 316, preferably following a basal plane. Trial buttress member 302 is joined with trial affixation member 312 by a bar 322 carried by the trial buttress member 302 and engaged with a channel 324 within the trial affixation member 312. In the present embodiment, bar 322 is journaled for rotation within channel 324, about a transverse axis of rotation T, to enable movement of the trial buttress member 302 and the trial affixation member 312 through a range of relative angular positions for selecting an appropriate relative angular position between the trial buttress member 302 and the trial affixation member 312 and, consequently, between the trial buttress surface 304 and the trial basal surface 316.

A restraining mechanism precludes inadvertent relative angular movement between the trial buttress member 302 and the trial affixation member 312 and comprises a detent arrangement 330 having a plurality of first detent elements in the form of teeth 332 carried by trial buttress member 302, spaced circumferentially about transverse axis of rotation T, and a second detent element in the form of a projection 334 carried by a resiliently flexible cantilever arm 336 located on the trial affixation member 312 so that the flexible cantilever arm 336 biases the projection into engagement with particular teeth 332, between adjacent particular teeth 332, to retain the trial buttress member 302 and the trial affixation member 312 in any one of several relative angular positions defined by the spacing between adjacent teeth 332. In this manner, precise predetermined relative angular positions are established between the trial buttress member 302 and the trial affixation member 312, positively defined by fixed increments of rotation between adjacent selectable relative angular positions and retained in a more positive fashion for increased ease and accuracy in subsequently matching the relative angular position of the buttress member 52 and the affixation member 62 of augment 50 to the relative angular position determined between the trial buttress member 302 and the trial affixation member 312 of the trial augment 300. The trial buttress member 302 and the trial affixation member 312 are indexed readily among the selectable relative angular positions merely by overcoming the biasing force exerted by the resiliently flexible cantilever arm 336.

Indicia in the form of a visible scale 350 on the trial buttress member 302 and a visible index mark 352 on the trial affixation member 312 provide a visible indication of the relative angular position between the trial affixation member 312 and the trial buttress member 302. The visible indication is located at the top 354 of the trial augment 300, rendering the indication highly visible for a quick and convenient determination of the relative angular position.

In instances where it is determined that augment 50 requires a buttress member which includes an extended further tab, such as tab 190 or 192 described above in connection with the embodiment illustrated in FIG. 18, trial augment 300 is provided with an extended trial supplemental tab 360 which emulates a tab 190 or 192. In the embodiment illustrated in FIG. 20, trial buttress member 302 emulates buttress member 52-3, and trial supplemental tab 360 emulates extended further tab 192. In the preferred construction, trial supplemental tab 360 is furnished in the form of a separate module selectively attached to trial buttress member 302 only when needed. To that end, trial buttress member 302 includes a selectively attached connection, shown in the form of a slot 362 for receiving a complementary tongue 364 of tab 360 in a fixed predetermined location on trial buttress member 302, and a post 366, having a head 368 spaced in an altitudinal direction above slot 362, integral with trial buttress member 302 and projecting into slot 362 for selective engagement with a keyhole aperture 370 in tongue 364 of tab 360.

Once seated and engaged beneath the head 368 of post 366, as indicated by the arrows 374 in FIG. 20, between a phantom depiction of the tab 360 detached from trial buttress member 302 and a full line depiction showing the tab 360 attached to trial buttress member 302, tab 360 is integrated with trial buttress member 302, firmly connected to trial buttress member 302, so that trial buttress member 302 emulates buttress member 52-3. Tab 360 is constructed of a malleable material, preferably a malleable metal, so that upon placement of trial augment 300 at the implant site 22 during a trialing procedure, as described above, attached tab 360 can be bent or otherwise deformed into a configuration wherein at least one of the simulated screw holes 376 is placed in an optimum position, in juxtaposition with the best available natural bone at the implant site 22. Extended further tab 192 then is bent or otherwise deformed into the same configuration to mimic the bent or otherwise deformed configuration of tab 360 so that upon placement of augment 50 at the implant site 22 the supplemental screw holes 194 of the augment 50 will be located appropriately for a secure attachment to available natural bone.

It will be seen that the present invention attains all of the objects and advantages summarized above, namely: Provides a system that enables a surgeon to select optimum compensation for an acetabular bone deficiency encountered at a particular acetabular implant site, and to do so intra-operatively, with increased accuracy, ease and dispatch, so as to minimize patient trauma; enables quick and effective compensation for acetabular bone deficiencies as an alternative to current procedures which require time-consuming preparation and use of structural allografts; provides a modular system for augmenting natural bone at an acetabular implant site during hip arthroplasty to compensate for deficiencies encountered in the natural bone at the implant site and thereby accommodate the needs of a particular patient accurately, without requiring a specific, custom-created implant component; enables the use of any of a wide range of currently available acetabular components, at an implant site augmented to compensate for conditions encountered at a particular implant site; expedites the completion of a hip arthroplasty, with increased ease and effectiveness, where augmentation of an acetabular implant site is necessary to compensate for conditions encountered at the implant site, and especially during a revision procedure; reduces trauma created by the conduct of hip arthroplasty, thereby promoting greater patient comfort and safety; promotes confidence on the part of an orthopedic surgeon in the accomplishment of a highly accurate, effective hip arthroplasty; conserves time and expense in completing an accurate and effective hip arthroplasty; provides an acetabular augmentation system having a high degree of versatility and exhibiting exceptional performance over an extended service life for encouraging widespread adoption and use.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An acetabular augment for compensating for a deficiency encountered in natural bone available at an implant site wherein, during a hip arthroplasty, the available natural bone is prepared so as to establish a prepared acetabulum for the reception of a conventional acetabular component having an outer surface with a conventional outer surface contour configuration, the prepared acetabulum having a contour configuration that extends along an acetabular envelope having a contour configuration complementary to the outer surface contour configuration of the conventional acetabular component and including a portion spaced from the available natural bone as a result of the encountered deficiency, the acetabular augment comprising:
   a buttress member having a buttress surface with a surface contour configuration complementary to the portion of the acetabular envelope spaced from the available natural bone;
   an affixation member having an affixation surface for affixing the affixation member to natural bone adjacent the prepared acetabulum; and
   a coupling arrangement for coupling the buttress member with the affixation member, affixed permanently at any selected one of a plurality of fixed angular positions relative to one another, the coupling arrangement including complementary coupling elements on the buttress member and on the affixation member for selective engagement to permanently affix the buttress member to the affixation member against movement of the buttress member relative to the affixation member when the buttress member and the affixation member are coupled at a selected one of the plurality of fixed angular positions, with the affixation surface permanently located at a corresponding selected angular position relative to the buttress surface so as to place the buttress surface in permanent secured juxtaposition with the acetabular envelope upon affixation of the affixation surface to the natural bone adjacent the prepared acetabulum, whereby the buttress surface will be located permanently to supplement the natural bone available at the prepared acetabulum for reception of the conventional acetabular component at the prepared acetabulum, with the outer surface of the acetabular component extending along the acetabular envelope, and the acetabular component supported by the available natural bone and the permanently secured buttress surface.

2. The acetabular augment of claim 1 wherein:
the prepared acetabulum has a predetermined central acetabular axis extending in a longitudinal direction;
the buttress surface has a central buttress axis extending in a substantially longitudinal direction for being placed in substantial alignment with the acetabular axis, upon juxtaposition of the buttress surface with the acetabular envelope; and
the coupling elements are selectively engageable along an engagement axis extending in a transverse direction spaced away from the buttress axis in a lateral direction, with the coupling elements located permanently at any selected one of a plurality of relative angular positions about the engagement axis to place the affixation surface permanently at the selected angular position relative to the buttress surface.

3. The acetabular augment of claim 2 wherein the coupling elements include complementary connector configurations establishing fixed angular increments between adjacent angular positions.

4. The acetabular augment of claim 3 including visible indicia on the buttress member and on the affixation member indicating selected angular positions of the affixation surface relative to the buttress surface.

5. The acetabular augment of claim 3 wherein the complementary connector configurations comprise interengageable splines spaced circumferentially about the engagement axis.

6. The acetabular augment of claim 5 including respective locking elements on the buttress member and the affixation member for selectively precluding relative movement between the buttress member and the affixation member in the transverse directions upon engagement of the coupling elements at a selected angular position between the buttress surface and the affixation surface.

7. The acetabular augment of claim 6 wherein:
the engagement elements include
a channel in one of the buttress member and the affixation member and extending along the transverse direction between opposite channel ends; and
a bar integral with another of the buttress member and the affixation member and extending along the transverse direction between opposite bar ends, the bar being engageable with the channel along the engagement axis to juxtapose the bar ends with corresponding channel ends; and the locking elements include
a groove located intermediate the opposite bar ends; and
a locking member mounted upon the affixation member intermediate the opposite channel ends for selective movement in lateral directions between an unlocked position, wherein the locking member is retracted for enabling movement of the bar along the channel in transverse directions to permit engagement of the engagement elements, and a locking position wherein upon engagement of the engagement elements and placement of the groove in registration with the locking member, the locking member is advanced into the groove to preclude movement between the bar and the channel along the transverse directions.

8. The acetabular augment of claim 7 wherein:
the bar is integral with the buttress member;
the channel extends within the affixation member; and
the locking member comprises a cam lock mounted within the affixation member for selective rotation about a longitudinal cam axis between the unlocked position, wherein the cam lock is retracted from the groove, and a locking position, wherein the cam lock is received within the groove.

9. The acetabular augment of claim 2 wherein the affixation member includes a basal surface for affixation to the natural bone adjacent the prepared acetabulum, and the engagement axis is spaced from the basal surface in a substantially longitudinal direction.

10. The acetabular augment of claim 9 wherein the basal surface extends in a basal plane extending substantially parallel to the engagement axis.

11. The acetabular augment of claim 9 wherein the affixation member includes at least two locator apertures extending through the affixation member at respective spaced-apart locator positions for locating the affixation member upon the natural bone adjacent the prepared acetabulum.

12. The acetabular augment of claim 1 including openings in the affixation member for securing the affixation member to natural bone adjacent the prepared acetabulum.

13. The acetabular augment of claim 1 including openings in the buttress member spaced from the buttress surface to secure the buttress member to natural bone adjacent the prepared acetabulum.

14. The acetabular augment of claim 13 including tabs integral with the buttress member for extending along natural bone adjacent the prepared acetabulum, the openings in the buttress member extending through the tabs for juxtaposition with the natural bone adjacent the prepared acetabulum.

15. The acetabular augment of claim 14 wherein at least one of the tabs is located for extending along further natural bone spaced farther away from the natural bone along which others of the tabs extend for juxtaposition of corresponding openings with the farther away natural bone.

16. A system for use in compensating for a deficiency encountered in natural bone available at an implant site wherein, during a hip arthroplasty, the available natural bone is prepared so as to establish a prepared acetabulum for the reception of a conventional acetabular component having an outer surface with a conventional outer surface contour configuration, the prepared acetabulum having a contour configuration that extends along an acetabular envelope having a contour configuration complementary to the outer surface contour configuration of the conventional acetabular component and including a portion spaced from the available natural bone as a result of the encountered deficiency, the system comprising:

a trial acetabular augment including
a trial buttress member having a trial buttress surface with a surface contour configuration complementary to the portion of the acetabular envelope spaced from the available natural bone;
a trial affixation member having an affixation surface for engaging natural bone adjacent the prepared acetabulum, the trial affixation member being coupled with the trial buttress member for selective angular movement relative to one another to enable selective placement of the trial affixation surface at a selected angular position relative to the trial buttress surface;
a restraining mechanism for restraining inadvertent relative angular movement between the trial affixation member and the trial buttress member away from the selected angular position of the trial affixation surface relative to the trial buttress surface;
a marking arrangement for establishing a marked location of the trial affixation member on the natural bone adjacent the prepared acetabulum;
a first indicator for indicating the selected angular position of the trial affixation surface relative to the trial buttress surface; and
an acetabular augment including
a buttress member having a buttress surface with a configuration that mimics the trial buttress surface;
an affixation member having an affixation surface with a configuration that mimics the trial affixation surface;
a coupling arrangement for coupling the affixation member to the buttress member, the coupling arrangement being configured for permanently affixing the affixation member against movement relative to the buttress member, at any selected one of a plurality of fixed angular positions relative to one another so as to enable matching the angular position indicated between the trial affixation surface and the trial buttress surface, to permanently affix the affixation surface at a selected angular position relative to the buttress surface and thereby mimic the selected relative angular position between the trial affixation surface and the trial buttress surface;
a second indicator for indicating the selected angular position of the affixation surface relative to the buttress surface;
a locator arrangement on the acetabular augment for locating the affixation member at the previously marked location of the trial affixation member to locate the buttress surface in juxtaposition with the acetabular envelope at the deficiency; and
an affixation arrangement on the acetabular augment for affixing the acetabular augment in place with the buttress surface juxtaposed with the portion of the acetabular envelope spaced from the available natural bone, and the affixation member affixed to the natural bone adjacent the prepared acetabulum.

17. The system of claim 16 wherein:
the prepared acetabulum has a predetermined central acetabular axis extending in a longitudinal direction;
the buttress surface has a central buttress axis extending in a substantially longitudinal direction for being placed in substantial alignment with the acetabular axis, upon juxtaposition of the buttress surface with the portion of the acetabular envelope spaced from the available natural bone;
the coupling elements are selectively engageable along an engagement axis extending in a transverse direction spaced away from the buttress axis in a lateral direction, with the coupling elements affixed permanently at any selected one of a plurality of relative angular positions about the engagement axis to place the affixation surface permanently at the selected angular position relative to the buttress surface;
the trial buttress surface has a central trial buttress axis extending in a substantially longitudinal direction for being placed in substantial alignment with the acetabular axis, upon juxtaposition of the trial buttress surface with the portion of the acetabular envelope spaced from the available natural bone; and
the trial affixation member and the trial buttress member are coupled for rotation about an axis of rotation extending in a transverse direction spaced away from the trial buttress axis in a lateral direction, for selective placement of the trial affixation surface at the selected angular position relative to the trial buttress surface.

18. The system of claim 17 wherein:
the coupling elements include complementary connector configurations establishing fixed angular increments between adjacent angular positions; and
the restraining mechanism includes complementary connector configurations on the trial buttress member and on the trial affixation member, and a fit between the complementary connector configurations establishing a bias against relative angular movement between the trial buttress member and the trial affixation member.

19. The system of claim 16 wherein:
the first indicator includes visible indicia on the buttress member and on the affixation member indicating selected angular positions of the affixation surface relative to the buttress surface; and
the second indicator includes visible indicia on the trial buttress member and on the trial affixation member indicating selected angular positions of the trial affixation surface relative to the trial buttress surface.

20. A trial acetabular augment for use in compensating for a deficiency encountered in natural bone available at an implant site wherein, during a hip arthroplasty, the available natural bone is prepared so as to establish a prepared acetabulum for the reception of a conventional acetabular component having an outer surface with a conventional outer surface contour configuration, the prepared acetabulum having a predetermined central acetabular axis extending in a longitudinal direction and a contour configuration that extends along an acetabular envelope having a contour configuration complementary to the outer surface contour configuration of the conventional acetabular component and including a portion spaced from the available natural bone as a result of the encountered deficiency, the trial acetabular augment comprising:
a trial buttress member having a trial buttress surface with a surface contour configuration complementary to the portion of the acetabular envelope spaced from the available natural bone;
a trial affixation member having an affixation surface for engaging natural bone adjacent the prepared acetabulum, the trial affixation member being coupled with the trial buttress member for selective angular movement relative to one another to enable selective placement of the trial affixation surface at a selected angular position relative to the trial buttress surface;
a restraining mechanism for restraining inadvertent relative angular movement between the trial affixation member and the trial buttress member away from the selected angular position of the trial affixation surface relative to the trial buttress surface, the restraining mechanism comprising a detent mechanism including a plurality of first detent elements on one of the trial buttress member and the trial affixation member, and a second detent element on the other of the trial buttress member and the trial affixation member, the first detent elements being spaced apart circumferentially about the axis of rotation, and the second detent element being biased into engagement with the first detent elements to establish fixed increments of rotation and corresponding fixed increments between adjacent angular positions between the trial buttress surface and the trial affixation surface;

a marking arrangement for establishing a marked location of the trial affixation member on the natural bone adjacent the prepared acetabulum; and an indicator for indicating the selected angular position of the trial affixation surface relative to the trial buttress surface;

wherein the first detent elements comprise teeth on the trial buttress member and the second detent element comprises a projection carried by a resilient arm on the trial affixation member, with the resilient arm biasing the projection into engagement with the teeth.

21. The trial acetabular augment of claim 20 wherein the indicator comprises visible indicia on the trial affixation member and on the trial buttress member, the visible indicia indicating the selected angular position of the trial affixation surface relative to the trial buttress surface.

22. The trial acetabular augment of claim 20 wherein the marking arrangement comprises at least two marking apertures extending through the trial affixation member at respective spaced-apart marking positions.

23. The trial acetabular augment of claim 20 including openings in the trial buttress member spaced from the trial buttress surface for indicating fastener locations.

24. The trial acetabular augment of claim 23 including at least one tab on the trial buttress member, at least one of the openings being located in the one tab.

25. The trial acetabular augment of claim 24 including a selectively attached connection between the one tab and the trial buttress member for enabling selective attachment of the one tab to the trial buttress member.

\* \* \* \* \*